(12) United States Patent
Sekimoto et al.

(10) Patent No.: US 6,642,202 B2
(45) Date of Patent: Nov. 4, 2003

(54) EGG HAVING ACTIVE OXYGEN ELIMINATING ABILITY AND METHOD OF PRODUCING SAME

(75) Inventors: Kunitoshi Sekimoto, Tokyo (JP); Akiko Matsuki, Kanagawa (JP); Ayuko Kashimori, Kyoto (JP)

(73) Assignee: Nosan Corporation, Kanagawa (JP)

( * ) Notice: Subject to any disclaimer, the term of this patent is extended or adjusted under 35 U.S.C. 154(b) by 0 days.

(21) Appl. No.: 10/096,291

(22) Filed: Mar. 12, 2002

(65) Prior Publication Data

US 2003/0175359 A1 Sep. 18, 2003

(51) Int. Cl.⁷ .................... A61K 38/00; A61K 35/54; A23B 5/00
(52) U.S. Cl. .................... 514/5; 424/581; 426/330.1
(58) Field of Search ............... 426/330.1; 424/581; 514/5

(56) References Cited

U.S. PATENT DOCUMENTS 5,130,155 A  *  7/1992  Yamate ................. 426/330.1
6,127,421 A  * 10/2000  Wideman, Jr. et al. ..... 514/565
6,177,121 B1 *  1/2001  Elkin et al. ............... 426/614

FOREIGN PATENT DOCUMENTS

EP          0 035 882      *  9/1981

* cited by examiner

*Primary Examiner*—Raymond Henley, III
(74) *Attorney, Agent, or Firm*—Fish & Richardson P.C.

(57) ABSTRACT

The object of the present invention is to allow an egg originally having almost no active oxygen eliminating ability, to strongly possess an active oxygen eliminating ability. It was found that an egg containing a high level of iodine (4.2 ppm or more) has an ability to eliminate active oxygen, which acts harmfully on the human body.

2 Claims, 1 Drawing Sheet

Mechanism of XYZ system low-level luminescence

EGG HAVING ACTIVE OXYGEN ELIMINATING ABILITY AND METHOD OF PRODUCING SAME

FIELD OF THE INVENTION

The present invention relates to a composition having an active oxygen eliminating ability, more specifically to a composition having an active oxygen eliminating ability that comprises, as an active ingredient, an egg from Aves containing iodine.

BACKGROUND OF THE INVENTION

It is conventionally said that active oxygen has a harmful toxicity against vital tissues, and is considered to be an important cause of the development of various diseases such as skin aging, cancers, apoplectic stroke, rheumatism, etc. (Seikagaku Jiten (Biochemical Dictionary), the $2^{nd}$ edition, p.699, Feb. 5, 1991, Tokyo Kagaku Dozin Co., Ltd.; Iwanami Rikagaku Jiten (Iwanami Physical and Chemical Dictionary), the $3^{rd}$ edition (enlarged edition), p.749, Feb. 20, 1986; U.S. Pat. No. 4,022,224; Japanese Patent Application Laying-Open (Kokai) No. 63-79834)

Examples of active oxygen known to be generated in vivo include superoxide anion radical, hydrogen peroxide, hydroxy radical, single oxygen, and peroxy radical or alkoxy radical that is generated by hyperoxidation of lipids. It is known that these active oxygens bring about crosslinking of collagen fibers, damage to DNA molecules, or damage to tissues due to chain radical generation, against the organism, and as a result, these become causes for aging of skin or body, elicitation of inflammation, damage to the smooth muscle in myocardial infarct, hepatopathy, dementia due to disruption of brain tissues, or provocation of cancerogenesis.

Accordingly, it is considered that elimination of active oxygen generated in vivo is important for prevention or treatment of these diseases. It is considered that especially elderly people have a degraded biophylactic ability, which is an ability to protect the body from oxidation-stress disorder of DNA molecules, and so supplementation of an antioxidant substance from outside the body is necessary. In respect of a method of supplementing such a substance, there is a high expectation for the antioxidant action of many antioxidant substances such as polyphenol present in foods (Chojyushoku no Science (Science of Longevity Food), p.223, Sep. 29, 2000, Science Forum Co., Ltd.)

From this viewpoint, the search for a substance which eliminates active oxygen has been performed broadly.

Japanese Patent Examined Publication (Kokoku) No.5-19531 discloses an active oxygen controlling composition, which is obtained by adding microorganisms to plant seeds or embryos roasted with far infrared radiation for fermentation, and further adding vegetable oil obtained from roasted plants thereto. Plants exemplified in this publication are grain crops such as rice, wheat and barley, and pulses such as soybean and corn. Moreover, Japanese Patent Application Laying-Open (Kokai) No. 6-128121 discloses that a water extract or organic solvent extract of Asparathus linearis water has an active oxygen eliminating action.

Thus, various things have been proposed, which control the action of active oxygen, but these are mainly natural materials, extracts or additives thereof. In respect of livestock products, there is only a report indicating that products from livestock, to which extruder-processed soybean-mixed feed were provided, have an active oxygen eliminating action, a product which was developed by the inventor (Japanese Patent Application No. 2000-231016). This indicates that an active oxygen eliminating ability is observed in products from livestock, when livestock were fed with feed mixed with raw materials having an active oxygen eliminating ability, but this does not refer to livestock products obtained by feeding livestock with feed mixed with raw materials not having an active oxygen eliminating ability.

Furthermore, techniques of allowing livestock products to have a functionality by devising feed are disclosed in Japanese Patent Application Laying-Open (Kokai) Nos. 2000-125781, 11-155495 and 10-056978. However, livestock products having an active oxygen eliminating ability, which are obtained as a result of mixing raw materials not having an active oxygen eliminating ability, into feed, have not been disclosed in any of these publications regarding prior art.

SUMMARY OF THE INVENTION

The object of the present invention is to impart to eggs originally having almost no active oxygen eliminating ability, a strong active oxygen eliminating ability.

While the present inventors, in connection with eggs, essential foods in daily life, have studied about the effect of minor components added to feed on an egg component and the effect of the egg component on life habit diseases, they have found that an egg containing a high level of iodine has an ability to eliminate active oxygen which harmfully acts on the human body.

That is to say, the present invention relates to,
(1) A composition for elimination of active oxygen which comprises, as an active ingredient, an egg having 4.2 ppm or more iodine,
(2) A food or drink which comprises the composition for elimination of active oxygen according to (1) above,
(3) A method for producing an egg for elimination of active oxygen, which comprises administration of more than a certain amount of iodine compound and/or seaweed to Aves, so that an egg thereof comprises 4.2 ppm or more iodine, and
(4) The production method according to (3) above, wherein the iodine compound is one or more selected from calcium iodate, potassium iodate and potassium iodide.

An active ingredient of the composition of the present invention, "an egg containing a high level of iodine", can generally be obtained as follows.

An iodine compound such as calcium iodate, potassium iodate, potassium iodide, sodium iodate, thymol iodide, copper iodide, diiodo salicylate or calcium periodate; seaweed containing a large amount of iodine such as Laminaria or kelp; or a processed product thereof is mixed into feed at more than a certain amount, and then the mixture is administered to Aves so as to increase the content of iodine in an egg thereof. In this case, it is preferable to use one or more selected from calcium iodate, potassium iodate and potassium iodide in terms of health of birds, transfer rate of iodine into eggs thereof, etc., and it is further preferable to use seaweed such as Laminaria in combination.

The amount of iodine administered to Aves depends on types of Aves, i.e. fowls, quails, etc., but in the case of an egg-laying hen, about 5 to 250 mg, preferably about 5 to 15 mg per hen per day may be administered. Generally, iodine is mixed into feed for administration, and in that case, estimating that a hen consumes about 100 g of feed per day, 50 to 2,500 ppm, desirably 50 to 150 ppm of iodine may be mixed into the feed.

As stated above, where a substance containing a large amount of iodine was administered to Aves, an egg containing a large amount of iodine of interest is laid after about a week. In the case of an egg-laying hen, for example, where feed containing about 50 ppm of iodine is administered, an egg containing about 300 μg of iodine can be obtained, and where feed containing about 100 ppm of iodine is administered thereto, an egg containing about 600 to 800 μg of iodine can be obtained.

Usually, the amount of iodine required for an egg-laying hen is 0.30 to 0.35 mg per kg of feed (according to NRC), and the actual amount of iodine in commercially available feed is 0.3 to 2.0 mg/kg. The amount of iodine in a ordinary egg laid from a hen fed with this commercially available feed is about 6 μg (according to the American Egg Board), and at most, the amount is about 30 μg per egg. Almost no active oxygen eliminating ability is observed in such a ordinary egg. When compared with this normal egg, since the egg obtained as above contains a remarkably high level of iodine, it has an active oxygen eliminating ability.

The thus obtained egg containing a high level of iodine can be used as the composition of the present invention, as is, or can be subjected to a processing such as heating, drying, concentration, pulverization or granulation. Moreover, it can be used in a form of a tablet, powder, etc. by mixing various excipients or binders, or can be processed to syrup, drink etc.

Since the composition of the present invention is nutritively excellent, having no side effects, continuous consumption is desired. Where the content of iodine per egg is set at 300 μg to 1,000 μg and then about 1 or 2 eggs are consumed per day, it is extremely easy to consume the composition of the present invention in daily life.

Since the weight of a commercially distributed shell egg is 58 g to 76 g and the weight of an eatable portion thereof is 50 g to 72 g, the content of iodine of 300 μg to 1,000 μg can be equal to the concentration of iodine of 4.2 ppm to 20.0 ppm. In a case where the concentration of iodine is 4.2 ppm or lower, though there is an active oxygen eliminating ability, it is not effective. In contrast, in a case where the concentration is 20.0 ppm or higher, egg-laying rate is decreased, resulting in a diminished feed efficiency.

Examples of Aves in the present invention include quails, silky fowls, etc. as well as fowls.

The term "composition" in the present invention may be used to mean an egg itself or a mixture of an egg and other substances.

DETAILED DESCRIPTION OF THE INVENTION

Figure 1:
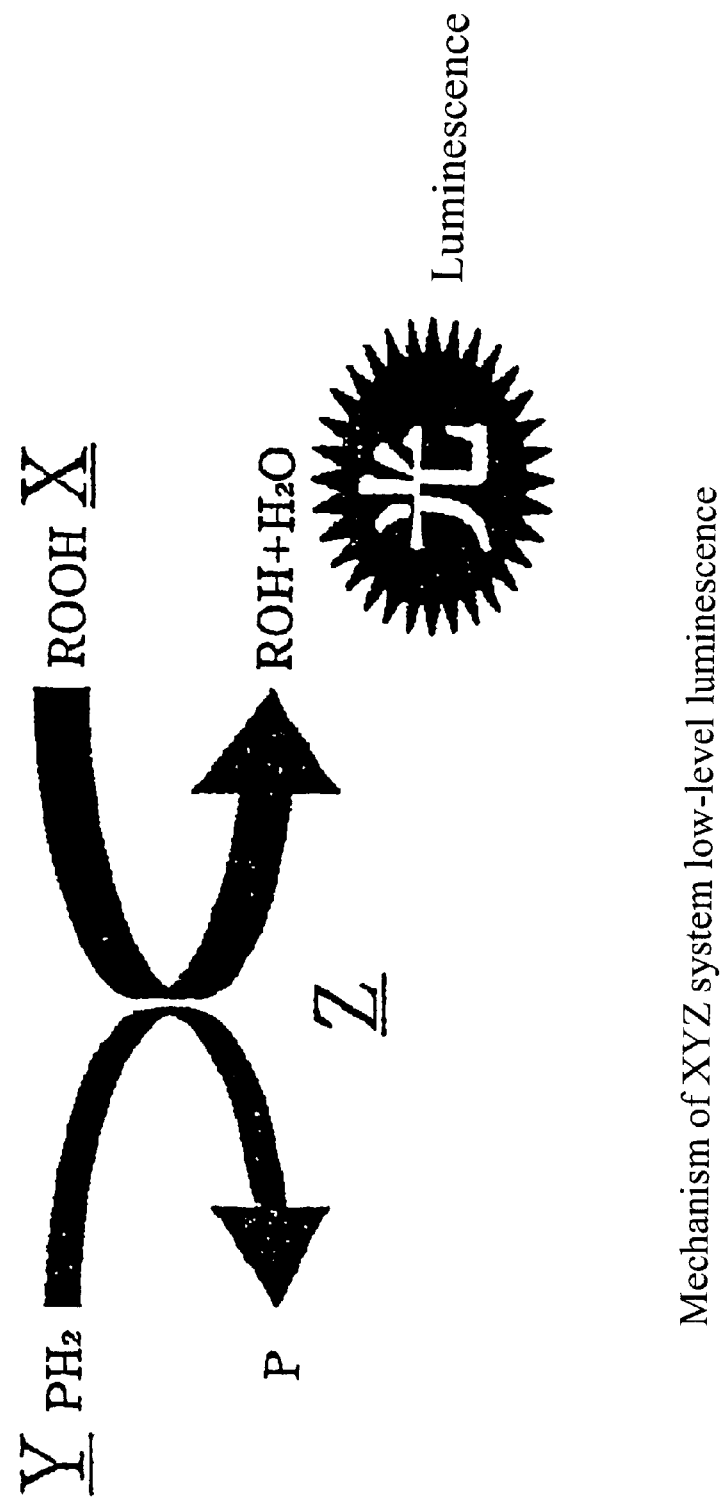
FIG. 1 is a FIGURE showing the mechanism of "XYZ system low-level luminescence".

The present invention is further described in the following examples. The examples are provided for illustrative purposes only, and are not intended to limit the scope of the invention.

EXAMPLES

Calcium iodate was added to commercially available feed for fowls so that the amount of iodine becomes 100 ppm, and then the obtained feed was provided to 100 egg-laying hens for feeding.

Low-level luminescence methods have been studied and developed as means for assaying active oxygen, and there is a publicly known assay of peroxide lipid or superoxide which involves the use of a luminescent reagent (luminol lucigenin), detection of single oxygen by low-level luminescence determination of 1,280 nm, etc. In recent years, Okubo et al. have clarified that natural radical eliminating substances such as flavonoid emits a feeble luminescence in the presence of hydrogen peroxide and acetaldehyde. Since this feeble luminescence is emitted as XYZ low-level luminescence in the presence of all the 3 species of active oxygen species (X), electron donor (Y) and receptor species (Z), Okubo et al. enabled an easy and simple screening of foods having an active oxygen eliminating function.

That is to say, a component generating active oxygen in vivo is defined as X component and an antioxidant component eliminating natural radicals (e.g. active oxygen, etc.) is defined as Y component. Elimination of active oxygen is not performed only in the presence of an antioxidant component (Y component), and Okubo et al. have found that the presence of a component enhances elimination reaction as a catalyst. This component is defined as Z component (FIG. 1).

For determination of active oxygen eliminating ability, luminance of this XYZ system low-level luminescence was used. Test Examples are shown as follows.

Text Example 1.

First, 4 holes of the first line in a 12-hole plate (4 holes×3 lines) were set as blanks (controls regarding luminance). 1 ml of raw solution obtained by breaking "an egg containing a high level of iodine" and homogenizing it without dividing into albumen and yolk, was poured into the second line, and 1 ml of raw solution of a ordinary egg processed in the same manner as with the second line, was poured into the third line (controls). Then, 1 ml of butyl alcohol, 1 ml of 2% hydrogen peroxide (X reagent), and 1 ml of saturated gallic acid solution (Y reagent) were added to all of the holes. The thus prepared plate was placed into a test chamber equipped with a VIM camera (Hamamatsu Photonics K.K.), and low-level luminescence resulting from the reaction was photographed after 10 minutes, so that the ability of an egg containing a high level of iodine as receptor species (Z) was evaluated depending on luminance of. XYZ system low-level luminescence. As shown in the results of Table 1, it was clarified that the test group has a remarkable predisposition as receptor species (Z) when compared with the control group.

Consequently, this test shows that "an egg containing a high level of iodine" has an active oxygen eliminating ability.

TABLE 1

Comparison of intensity of XYZ eliminating luminescence

|  | Z component | | | |
| --- | --- | --- | --- | --- |
| Luminance control group | – | – | – | – |
| Test group | + + + + + | + + + + | + + + + + | + + + + |
| Control group | + | + + | + + | + + |

Test Example 2.

Eight holes of the first line in a 96-hole plate (8 holes×12 lines) were set as blanks (controls regarding luminance). 0.5 ml of sample obtained by breaking "an egg containing a high level of iodine", homogenizing it without dividing into albumen and yolk, and being subjected to two folded dilution ($\times 2^0$ to $2^9$) was poured into the second line, and further 0.5 ml of raw solution of a ordinary egg processed in the same manner as for the second lines was poured into the third line and the other remaining lines (controls). Then, 0.5 ml of butyl alcohol and 0.5 ml of 2% hydrogen peroxide (X reagent) were added to all of the holes. The thus prepared plate was placed into a test chamber which was equipped with a VIM camera (Hamamatsu Photonics K.K.), and low-level luminescence resulting from reaction was photographed after 10 minutes, so that the degree of active oxygen eliminating ability of "an egg containing a high level of iodine" was evaluated depending on luminance of XYZ system low-level luminescence. The results are shown in Table 2. The table clearly shows that, when compared with the control group, the test group, that is, "an egg containing a high level of iodine" has a high active oxygen eliminating ability.

TABLE 2

Comparison of active oxygen eliminating ability (1)

| | $2^0$ | $2^{-1}$ | $2^{-2}$ | $2^{-3}$ | $2^{-4}$ | $2^{-5}$ | $2^{-6}$ | $2^{-7}$ | $2^{-8}$ | $2^{-9}$ | Luminance Control (blank) | Luminance Control (only reagent) |
|---|---|---|---|---|---|---|---|---|---|---|---|---|
| Test group | +++ | +++ | +++ | +++ | +++ | +++ | +++ | +++ | +++ | +++ | − | ± |
|  | ++ | +++ | ++ | ++ | + | + |  |  | + |  |  |  |
| Control group | ++ | ++ | ++ | + | + | + | ± | ± | ± | ± | − | ± |

Test Example 3.

Similarly, a test was performed for comparison of active oxygen eliminating ability between feed for hens laying ordinary eggs and feed for "eggs containing a high level of iodine". Setting as blanks 3 holes of the first line in a 12-hole plate (3 holes×4 lines), 1 ml of feed for ordinary eggs was poured into 3 holes of the second line, and 1 ml of feed for eggs containing a high level of iodine was poured into the third line. The final line was set as a positive control, and 1 ml of the feed mixed with soybeans processed with the extruder described in Japanese Patent Application No. 2000-231016, which was proposed by the present applicant (corn 50, milo 5, barley 10, soybean cake 10, extruder-processed soybean 15, molasses 2, rice bran 5, common salt 0.3, calcium carbonate 1.2, calcium phosphate 1.1, a mixture of vitamin and mineral 0.4) was poured thereinto. Then, 2 ml of butyl alcohol and 2 ml of 2% hydrogen peroxide (X reagent) were added to all of the holes. The results are shown in Table 3.

Low-level luminescence indicating an active oxygen eliminating ability was not observed in both feed for ordinary eggs and feed for "eggs containing a high level of iodine".

This result indicates that "eggs containing a high level of iodine" comes to have an active oxygen eliminating ability as shown in Test Examples 1 and 2, although the active oxygen eliminating ability was not observed in feed.

TABLE 3

Comparison of active oxygen eliminating ability (2)

| Blank | Normal feed | Feed for hens laying eggs containing a high level of iodine | Positive control |
|---|---|---|---|
| − | ± | ± | + + + + |
| − | ± | ± | + + + + + |
| − | ± | ± | + + + + |
| − | ± | ± | + + + + |

Effect of the Invention

The present invention allows raw materials having no active oxygen eliminating ability to possess an active oxygen eliminating ability, and enables prevention of the detrimental effect of active oxygen.

What is claimed is:

1. A method of eliminating active oxygen comprising:

providing to a human subject an avian egg having 4.2 ppm or more iodine to eliminate active oxygen from the human body.

2. The method of claim 1, wherein the egg has iodine in the range of 4.2 ppm to 20 ppm.

\* \* \* \* \*